United States Patent
Christensen

(10) Patent No.: US 9,764,139 B2
(45) Date of Patent: Sep. 19, 2017

(54) PRE-IMPLANT DETECTION

(71) Applicant: Medtronic, Inc., Minneapolis, MN (US)

(72) Inventor: Eric M. Christensen, Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 689 days.

(21) Appl. No.: 14/162,869

(22) Filed: Jan. 24, 2014

(65) Prior Publication Data

US 2015/0209588 A1    Jul. 30, 2015

(51) Int. Cl.
*A61N 1/36* (2006.01)
*A61N 1/372* (2006.01)

(52) U.S. Cl.
CPC ......... *A61N 1/36128* (2013.01); *A61N 1/372* (2013.01); *A61N 1/37252* (2013.01); *A61N 1/37211* (2013.01); *A61N 2001/37294* (2013.01)

(58) Field of Classification Search
CPC .............. A61N 1/3756; A61N 1/36128; A61N 1/37252; A61N 2001/37294
See application file for complete search history.

(56) References Cited

U.S. PATENT DOCUMENTS

| | | | |
|---|---|---|---|
| 4,899,750 A | 2/1990 | Ekwall | |
| 5,534,018 A | 7/1996 | Wahlstrand et al. | |
| 5,876,353 A * | 3/1999 | Riff | A61B 5/0535 600/529 |
| 5,957,861 A | 9/1999 | Combs et al. | |
| 6,016,447 A | 1/2000 | Juran et al. | |
| 6,112,121 A | 8/2000 | Paul et al. | |
| 6,154,675 A | 11/2000 | Juran et al. | |
| 6,512,949 B1 * | 1/2003 | Combs | A61B 5/0535 600/547 |
| 6,659,981 B2 | 12/2003 | Stewart et al. | |
| 6,672,895 B2 | 1/2004 | Scheiner | |
| 6,675,049 B2 | 1/2004 | Thompson et al. | |
| 7,092,765 B2 | 8/2006 | Geske et al. | |
| 7,233,825 B2 | 6/2007 | Jorgenson et al. | |
| 7,647,124 B2 | 1/2010 | Williams | |
| 7,720,529 B1 * | 5/2010 | Schecter | A61B 5/7221 600/513 |
| 7,901,396 B2 | 3/2011 | Shah et al. | |

(Continued)

OTHER PUBLICATIONS (PCT/US2015/012336) PCT Notification of Transmittal of the International Search Report and the Opinion of the International Searching Authority, Mailed Mar. 26, 2015, 11 pages.

*Primary Examiner* — Sean Dougherty

(57) ABSTRACT

A medical device system and associated method determine an implantable medical device state prior to implantation. An impedance monitoring module monitors for a change in impedance between a pair of electrodes coupled to the impedance monitoring circuit. The system includes an enclosure for carrying the implantable medical device. The enclosure has a surface having an electrical impedance. A control module is configured to detect one of a first pre-implant state and a second pre-implant state of the implantable medical device in response to the impedance monitoring module detecting a change in impedance between the electrodes and adjust operation of the implantable medical device in response to detecting the impedance change.

29 Claims, 7 Drawing Sheets

(56) References Cited

U.S. PATENT DOCUMENTS

| | | | |
|---|---|---|---|
| 7,937,150 B2* | 5/2011 | Kuehn | A61B 5/053 607/28 |
| 7,991,467 B2 | 8/2011 | Markowitz et al. | |
| 8,140,159 B2* | 3/2012 | Inman | A61N 1/36082 607/27 |
| 8,262,672 B2 | 9/2012 | Neidert et al. | |
| 8,394,079 B2 | 3/2013 | Drake et al. | |
| 8,478,431 B2 | 7/2013 | Griswold et al. | |
| 8,630,719 B2* | 1/2014 | Eggen | A61N 1/05 607/115 |
| 2003/0100220 A1 | 5/2003 | Scheiner | |
| 2005/0137480 A1* | 6/2005 | Alt | A61B 5/0031 600/508 |
| 2006/0017575 A1* | 1/2006 | McAdams | A61B 5/0031 340/573.1 |
| 2006/0200039 A1* | 9/2006 | Brockway | A61B 5/053 600/547 |
| 2007/0119741 A1 | 5/2007 | Wenger et al. | |
| 2009/0264780 A1 | 10/2009 | Schilling | |
| 2009/0276004 A1 | 11/2009 | Kronich et al. | |
| 2010/0094252 A1 | 4/2010 | Wengreen et al. | |
| 2010/0113962 A1 | 5/2010 | Hettrick et al. | |
| 2010/0305579 A1 | 12/2010 | Williams et al. | |
| 2011/0201921 A1 | 8/2011 | Neidert et al. | |
| 2012/0109079 A1 | 5/2012 | Asleson et al. | |
| 2012/0283705 A1 | 11/2012 | Lee et al. | |
| 2012/0303078 A1* | 11/2012 | Li | A61N 1/3956 607/4 |
| 2013/0027186 A1 | 1/2013 | Cinbis | |
| 2013/0079798 A1 | 3/2013 | Tran et al. | |
| 2013/0123748 A1 | 5/2013 | Drake et al. | |
| 2013/0131591 A1 | 5/2013 | Berthiaume et al. | |
| 2013/0184654 A1 | 7/2013 | Drake et al. | |
| 2013/0253342 A1 | 9/2013 | Griswold et al. | |
| 2013/0253343 A1 | 9/2013 | Waldhauser et al. | |
| 2013/0253345 A1 | 9/2013 | Griswold et al. | |

* cited by examiner

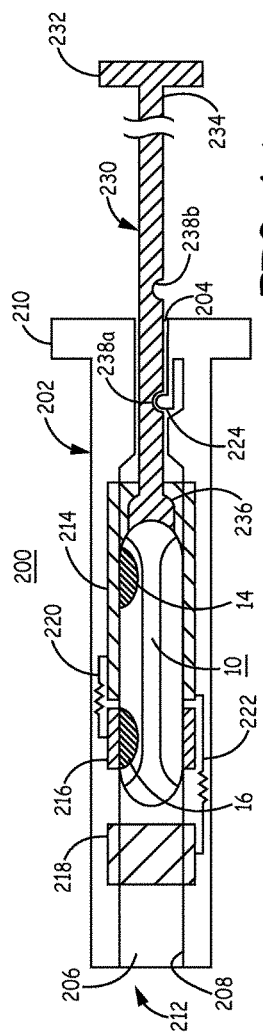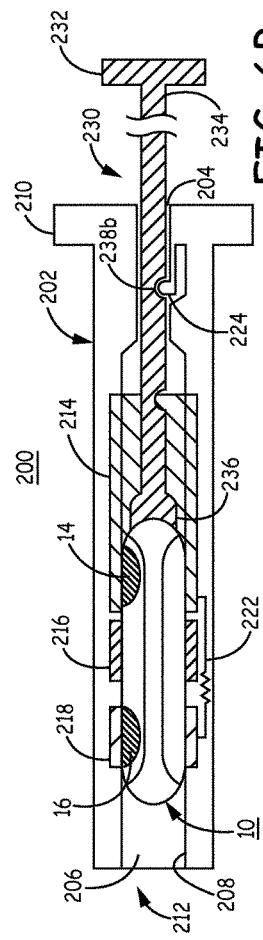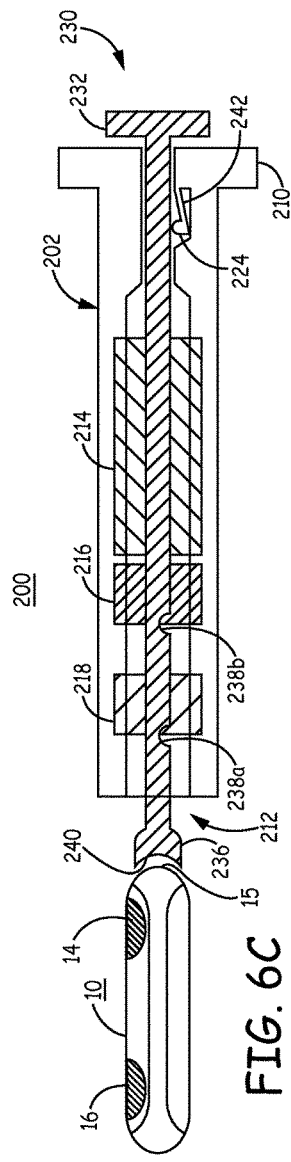

PRE-IMPLANT DETECTION

TECHNICAL FIELD

The disclosure relates generally to an implantable medical device (IMD) configured to detect various pre-implant conditions and delivery tools for implanting such devices.

BACKGROUND

Numerous implantable medical devices are available for acute or chronic implantation within patients. Some implantable medical devices may be used to chronically monitor physiological signals of the patient, such as implantable hemodynamic monitors, implantable cardiac monitors (sometimes referred to as implantable loop recorders or ECG monitors), implantable blood chemistry monitors, implantable pressure monitors, or the like. Other implantable devices may be configured to deliver a therapy in conjunction with or separate from the monitoring of physiological signals.

Advances in medical device technology have enabled implantable devices to be made smaller in size, which facilitates minimally invasive procedures for implanting the device and promotes patient comfort. Reduction of device size, however, poses limitations on the space available for batteries, telemetry communication modules, and other device components that support the primary device function. For example, replacing a bi-directional telemetry communication module in a device that does not necessarily require two-way communication for receiving programming commands with a smaller one-way transmission telemetry communication module can save space allowing significant device size reduction. The one-way transmission enables a device, such as a monitoring device, to transmit physiological signal data collected by the device.

Without bi-directional communication capabilities, however, testing and confirmation of the operability of the implantable device upon command, e.g. prior to implantation, is generally not possible. A need exists, therefore, for implantable medical device systems that enable size reductions, for example by implementing transmission-only telemetry communication modules, while still providing an implanting clinician and patient with the ability to confirm the operability or status of a medical device prior to implantation.

BRIEF DESCRIPTION OF THE DRAWINGS

FIGS. 6A-6C are sectional views of various stages or positions of an implant tool for implanting an IMD.

DETAILED DESCRIPTION

Figure 1:
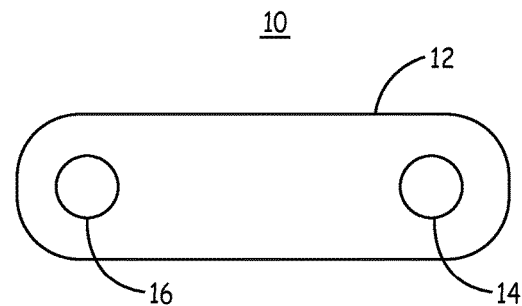
FIG. 1 is a conceptual diagram of an example IMD.

FIG. 1 is a conceptual diagram of an example IMD 10. IMD 10 is shown embodied as an injectable monitoring device having a proximal electrode 14 and a distal electrode 16 located along an IMD housing 12. IMD housing 12 encloses electronic circuitry and protects circuitry from body fluids. For example, IMD 10 may be embodied as an implantable cardiac monitor wherein electrodes 14 and 16 are used to sense ECG signals extra-thoracically, for example sub-muscularly or subcutaneously. ECG signals may be stored in memory of IMD 10, and ECG data may be transmitted by IMD 10 to another device, which may be another implantable device or an external device.

The configuration illustrated in FIG. 1 is just one example configuration. In other instances, sensing electrodes 14 and 16 may be located at other positions along IMD housing 12 than the positions shown in FIG. 1. For example, the electrodes 14 and 16 are shown both positioned along a top side of IMD 10, but in other examples electrodes 14 and 16 may be located on the bottom side or lateral side of IMD 10, on opposing sides of IMD 10, or on one or both ends of IMD 10. Additionally, all or a portion of housing 12 may function as one of the electrodes and be insulated from any other electrodes positioned along housing 12. In still other embodiments, an IMD system may include one or more electrodes carried by an electrical lead or tether extending away from the IMD and coupled to the IMD internal circuitry via electrical conductors. In further instances, IMD 10 may include more than two electrodes.

Although illustrated and described throughout this disclosure as being a cardiac monitor, IMD 10 may be any of number of other implantable devices, including implantable hemodynamic monitors, implantable blood chemistry monitors, implantable pressure monitors, or the like. In these cases, IMD 10 may include additional sensors to monitor the desired physiological signal.

Figure 2:
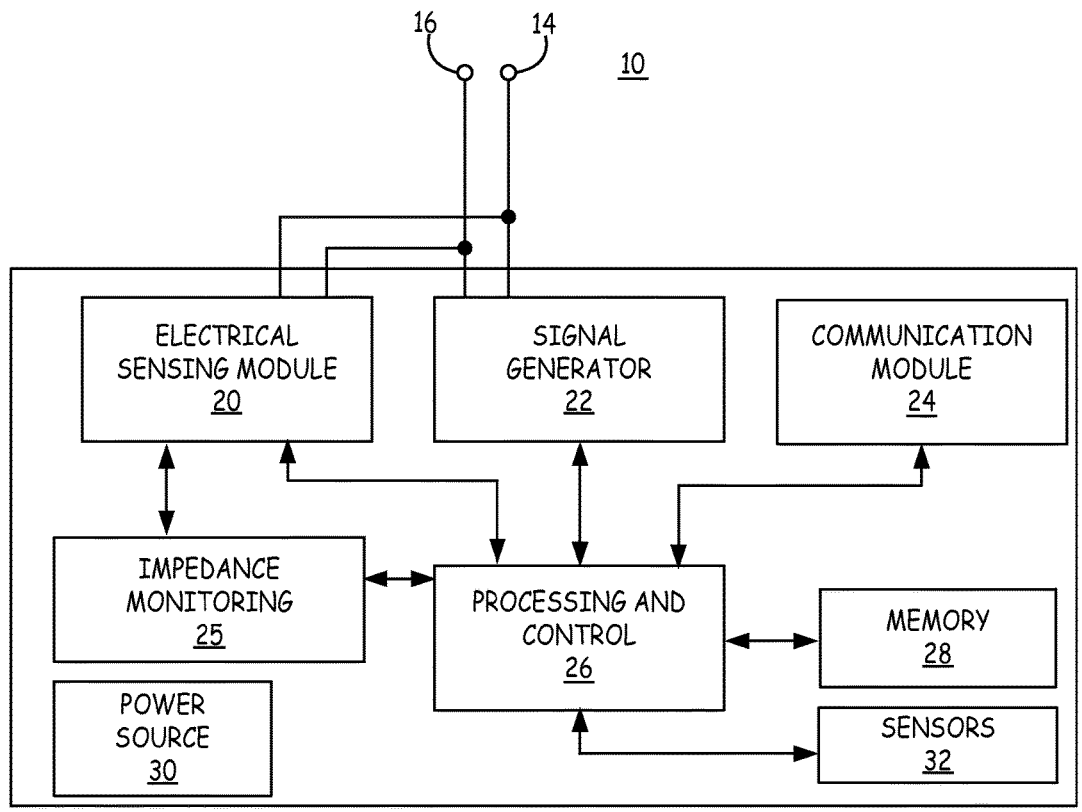
FIG. 2 is a functional block diagram of the IMD shown in FIG. 1.

FIG. 2 is a functional block diagram of IMD 10 shown in FIG. 1. IMD 10 includes an electrical sensing module 20 coupled to electrodes 14 and 16 for sensing electrical signals within a patient, e.g. ECG signals, EEG signals, EMG signals, or other desired physiological signals. IMD 10 may be embodied as a monitoring only device without therapy delivery capabilities. In other examples, IMD 10 may include a signal generator 22 coupled to electrodes 14 and 16 for delivering electrical pulses to achieve a therapeutic benefit to the patient in addition to or instead of monitoring physiological signals of the patient. IMD 10 includes a processing and control module 26 and associated memory 28 for controlling IMD functions and processing signals received from electrodes 14 and 16. IMD 10 may include other optional sensors 32 for monitoring physiological signals, such as an activity sensor, pressure sensor, oxygen sensor, accelerometer, or other sensor used to monitor a patient.

Processing and control module 26 may control monitoring time periods according to a particular clinical application, digitize electrical signals received by electrodes 14 and 16 and/or perform any desired processing on the electrical signals to generate electrical signal data, and store electrical signal data in memory 28. Communication module 24 includes an antenna and wireless transmitter to transmit electrical signal data, e.g. ECG signal data, stored in memory 28 or received from processing and control module 26 in real time. According to some examples, communication module 24 is provided with one-way transmission capabilities. Communication module 24 may be configured to transmit communication signals via inductive coupling, electromagnetic coupling, tissue conductance, Near Field Communication (NFC), Radio Frequency Identification (RFID), BLUETOOTH® Low Energy or other proprietary or non-proprietary wireless telemetry communication schemes.

The techniques disclosed herein may be used in a transmitting-only device that is unable to receive a wake-up signal, interrogation command or other request from another device for establishing IMD status prior to implantation in a patient's body. In alternative embodiments, communication module 24 may include a receiver for receiving wireless communication signals in addition to the transmitter or a transceiver to enable two-way communication. In the case of two-way communication, the techniques of this disclosure may reduce battery consumption during implant as IMD 10 would not need to monitor for a wake-up signal, interrogation command or other request from another device prior to implant.

A power source 30 provides power to each of the modules 20, 22, 24, 25, 26, 28 and 32 as needed. Power source 30 may include one or more energy storage devices, such as one or more rechargeable or non-rechargeable batteries.

Impedance monitoring module 25 is coupled to electrodes 14 and 16, directly or via sensing module 20, for measuring the impedance between electrodes 14 and 16. Impedance monitoring module 25 may include a drive signal source for applying a voltage or current signal across electrodes 14 and 16 for measuring the impedance between electrodes 14 and 16. For example, a very short, low level current pulse could be applied periodically to enable a voltage measurement across electrodes 14 and 16.

The term impedance as used herein is not intended to exclude resistance-only measurements but rather to convey the use of measuring any electrical impedance or component thereof which enables distinguishing between pre-implant states. Examples of impedance measuring circuits or methods that could be implemented in module 25 for monitoring impedance are generally described in commonly-assigned U.S. Pat. No. 4,899,750 (Ekwall), U.S. Pat. No. 5,957,861 (Combs et al.), and pre-grant U.S. Publication No. 2010/0113962 (Hettrick, et al.), all of which are hereby incorporated herein by reference in their entirety.

Impedance monitoring module 25 is controlled by processing and control module 26 to periodically measure the impedance between electrodes 14 and 16. In response to the measured impedance, processing and control module 26 may detect one of two pre-implant states, referred to herein as a shipping state and a pending-implant state. While only two pre-implant states are described in the illustrative embodiments presented herein, it is contemplated that in other embodiments more than two pre-implant states could be defined and detected.

Processing and control module 26 is configured to respond to a change from the shipping state to the pending-implant state by generating a pending-implant state confirmation signal indicating the IMD 10 is operable and ready for implant. This confirmation signal may be a signal transmitted from communication module 24 to an external device. In other instances, the generated signal may be an audible, tactile or visual indicator as described below.

In some embodiments, IMD 10 may be further configured to detect an implant state of IMD 10 based on impedance between electrodes 14 and 16. Processing and control 26 may be configured to respond to a change from a pre-implant state to the implant state by initiating normal operating functions, which may include, for example, initial self-diagnostic testing and launching normal operating functions such as physiological signal monitoring and/or therapy. Examples of methods that may be used to detect an implant state are generally disclosed in commonly-assigned U.S. Pat. No. 5,534,018 (Wahlstrand, et al.), U.S. Pat. No. 6,016,447 (Juran et al.) and U.S. Pat. No. 7,991,467 (Markowitz, et al.), all of which references are incorporated herein by reference in their entirety.

IMD 10 is configured to be shipped in the shipping state associated with a known shipping impedance. The shipping state is a minimal power state (sometimes referred to as an "off" or "sleep" state) with a majority of device circuitry powered down to minimize power consumption. A clock or other timing device included in processing and control module 26 may be used to control impedance monitoring module 25 to periodically measure the impedance across electrodes 14 and 16.

As will be described in greater detail below, IMD 10 may be re-positioned or adjusted relative to an enclosure, such as a packaging tray or an implant or delivery tool, such that, prior to implantation, electrodes 14 and 16 are coupled to a known impedance different than the shipping impedance, which signifies a pending-implant state. Upon detecting the pending-implant impedance, processing and control module 26 generates a signal that is transmitted by communication module 24 to notify the clinician that the IMD 10 is in an operable state.

In this way, a clinician will be assured that the IMD 10 is operating properly prior to making a skin incision or starting surgical procedures for implanting the IMD 10. When communication module 24 is implemented as a one-directional transmitter without signal reception, the confirmation of the operability of the IMD 10 prior to implantation cannot be performed using an interrogation or wake-up command from a programmer. The detection of a pending-implant state by impedance monitoring module 25 and a subsequent signal transmission by communication module 24 provides this confirmation to the clinician.

Modules 20, 22, 24, 25, 26, 28, 30 and 32 represent functionality included in IMD 10. Modules of the present disclosure may include any discrete and/or integrated electronic circuit components that implement analog and/or digital circuits capable of performing the functions attributed to the modules herein. For example, the modules may include analog circuits, e.g., amplification circuits, filtering circuits, and/or other signal conditioning circuits. The modules may also include digital circuits, e.g., combinational or sequential logic circuits, integrated circuits, a processor (shared, dedicated, or group) that executes one or more software or firmware programs, memory devices, or any other suitable components or combination thereof that provide the described functionality.

Memory 28 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), Flash memory, or any other memory device. Memory 28 may include non-transitory computer readable storage media storing instructions that, when executed by one or more processing circuits, cause the modules to perform various functions attributed to IMD 10. The storage media may include any computer-readable storage media with the sole exception being a transitory, propagating signal.

Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components.

Figure 3A:
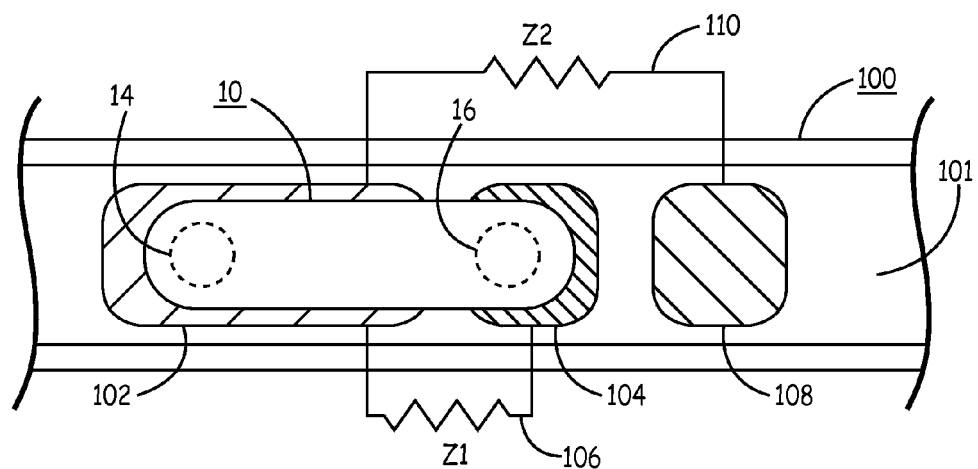
FIGS. 3A and 3B are schematic diagrams of an enclosure for receiving and retaining an IMD, for example during shipping and prior to implantation of the IMD.
Figure 3B:
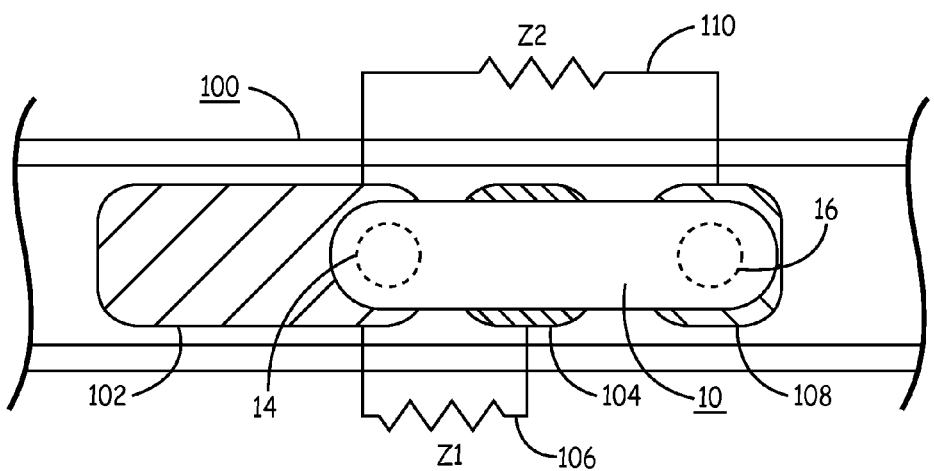

FIGS. 3A and 3B are schematic diagrams of an enclosure 100 for receiving and retaining IMD 10 prior to implantation of IMD 10 in the body of a patient. Enclosure 100 may be embodied as an enclosure into which IMD 10 is inserted at the time of manufacture in a first position, also referred to herein as a shipping position. Enclosure 100 may be embodied as a packaging tray that is used to retain IMD 10 in the shipping position. Enclosure 100 may alternatively be embodied as an implant tool in which IMD 10 is pre-loaded in a first, shipping position at the time of packaging IMD 10 at a manufacturing facility. IMD 10 is adjusted to a second, pending-implant position, associated with a pending-implant impedance, just prior to implantation. According to various examples described below in conjunction with FIGS. 4-9, enclosure 100 may be a packaging tray for retaining IMD 10 prior to implant in some examples and an implant tool used to implant IMD 10 in other examples or any combination of the various enclosures described herein.

In the example of FIGS. 3A and 3B, enclosure 100 includes three contacts 102, 104, and 108 along an inner wall 101 of enclosure 100. In the shipping position, as shown in FIG. 3A, IMD 10 electrodes 14 and 16 are positioned in direct electrical contact with a first contact 102 and a second contact 104 having a known electrical impedance Z1 106 between contacts 102 and 104, shown schematically as Z1. In a second, pending-implant position, as shown in FIG. 3B, IMD 10 electrodes 14 and 16 are positioned in direct electrical contact with the first contact 102 and the third contact 108 having an electrical impedance 110 between contacts 102 and 108, shown schematically as Z2. While Z1 106 and Z2 110 are shown schematically using a resistor symbol, it is recognized that the impedances 106 and 110 may be implemented using numerous physical configurations that may or may not include a conventional discrete electrical resistor component. Examples of various physical configurations for implementing an electrical impedance between two contacts are described in greater detail below.

Contacts 102, 104 and 108 are arranged to mate with electrodes 14 and 16 positioned along one major side of IMD 10. It is recognized that contacts may be configured along a surface of enclosure 100 as needed to mate with electrodes positioned along different sides or combinations of sides of IMD 10.

Impedance Z1 106 applied between electrodes 14 and 16 when IMD 10 is positioned in the shipping position as shown in FIG. 3A is known to IMD 10 as a shipping impedance. While detecting the shipping impedance, IMD 10 operates in the shipping state, which is described above. IMD periodically measures the impedance between electrodes 14 and 16 to detect a change from the shipping impedance Z1 106. As long as there is no significant change in the impedance between electrodes 14 and 16, the IMD 10 will remain in the shipping state, which includes periodically measuring impedance between electrodes 14 and 16. The frequency of periodic impedance monitoring may be once every second, once every 5 seconds or other time period greater than or less than these examples and may vary between embodiments.

FIG. 3B is a schematic diagram of IMD 10 retained within enclosure 100 after being adjusted to a second position, also referred to herein as a pending-implant position. IMD 10 has been moved from the first position within enclosure 100 to the second position within enclosure 100 such that the proximal electrode 14 is still in direct electrical contact with the first elongated contact 102, but the distal electrode 16 is now in direct electrical contact with a third contact 108. The first contact 102 and the third contact 108 are characterized by a second, pending-implant impedance Z2 110 that is different than the first impedance Z1 106.

Upon detecting a change from Z1 106 to Z2 110 during a periodic impedance measurement, IMD 10 transitions from the shipping state to the pending-implant state. As described briefly above, IMD 10 may perform one or more operations in preparation for implantation during the pending implant state. For example, IMD 10 may transmit a pending-implant confirmation signal to an external device, which may be a physician programmer, a computer, or a handheld device, signaling that the IMD 10 has detected the pending-implant state and confirming that the IMD 10 is in operable condition. In this way, the clinician is notified that the IMD 10 is fully operable and in satisfactory condition for implantation. If a communication signal is not received by an external device upon adjusting the IMD 10 from the first, shipping position to the second, pending-implant position, this may be an indication that the IMD 10 is not operating satisfactorily for implantation. The clinician may select a different device to implant or postpone the surgical procedure prior to starting surgery. IMD 10 may perform additional operations upon detecting a pending implant state, such as self-diagnostic tests which may include a battery test, a memory check or other tests. IMD 10 may transmit a communication signal reporting a result(s) of any self-diagnostic test(s).

Both the shipping state and the pending-implant state may be referred to as pre-implant states since the IMD 10 is not required to fully power primary function capabilities, such as the intended physiological monitoring capabilities and/or therapy delivery functions. As such the pending-implant state may still be a minimally powered state or reduced powered state as compared to the fully operational implant state since only the operations of transmitting a pending-implant confirmation signal and any optional self-diagnostic tests need be performed. In other embodiments, upon detecting the pending-implant state, the IMD processing and control module 26 may transition IMD 10 to the fully-powered, normal operating state in anticipation of implantation of IMD 10.

In some examples, once the pending-implant confirmation signal is transmitted and any optional device diagnostic testing is performed, the IMD 10 may return to a minimally powered (or "off") state and remain in a minimal power state while still in the second, pending-implant position within enclosure 100 to conserve battery energy prior to implantation. In other examples, IMD 10 may remain in the pending state but not transmit any additional pending-implant confirmation signals after the initial pending implant confirmation signal is sent. Alternatively, the IMD 10 may continue to transmit a periodic "implant-ready" signal after the initial pending-implant confirmation signal as long as IMD 10 remains in the pending-implant position to notify the clinician that the IMD 10 is in operable condition and ready for implantation.

If an implant procedure is cancelled or delayed for other reasons, IMD 10 may be returned to the first, shipping position within enclosure 100. IMD 10 determines via impedance monitoring module 25 that the impedance again matches the shipping impedance and transitions back to the shipping state. If the IMD 10 is subsequently advanced to the second, pending-implant position, IMD 10 may again transmit the pending-implant confirmation signal to notify the clinician that the IMD 10 is in operable condition, including passing any of the optional self-diagnostic tests.

IMD 10 may be configured to detect another change in impedance between electrodes 14 and 16 during a subsequent impedance monitoring time period after implantation of IMD 10. The impedance measured by IMD 10 after implantation is an impedance corresponding to contact between electrodes 14 and 16 and body tissue and fluids. In response to detecting the impedance associated with body tissue and/or fluids, IMD 10 initiates the fully functional implant state. The implant state corresponds with the normal operating mode of IMD 10. If the self-diagnostic tests were not performed in the pending-implant state, IMD 10 may perform the self-diagnostics as part of the implant state. Additionally, IMD 10 begins to acquire physiological signals, process those signals, and transmit the signals in accordance with the pre-programmed operating parameters. The normal operation initiated upon detecting implantation of IMD 10 will vary between embodiments, according to a particular medical application for which IMD 10 is being used, which may include physiological signal monitoring, therapy delivery or a combination of both.

Accordingly, IMD 10 may be readily adjusted between two pre-implant states by shifting a position of IMD 10 between a shipping position corresponding to a first known impedance and a pending-implant position corresponding to a second known impedance. The first and second known impedances are selected to be recognizably different by the impedance monitoring module 25. The adjustment between the two pre-implant states may occur in both directions an unlimited number of times in some embodiments in that the IMD 10 may be returned to a shipping position from the pending-implant position, e.g. if a delay or cancellation of an implant procedure occurs.

It is recognized that in some instances IMD 10 may measure an impedance that does not correspond to either the shipping state or the pending-implant state during the transition from the shipping position to the pending-implant position. The IMD 10 may ignore an impedance measurement that does not correspond to known impedance values or ranges designated for each of the shipping and pending-implant states when impedance monitoring module 25 is measuring impedance for the detection of IMD pre-implant states.

The respective impedances Z1 and Z2 applied between contacts 102 and 104 and between contacts 102 and 108 may vary between embodiments as long as the difference between Z1 106 and Z2 110 is large enough to be easily detectable and distinguishable by the IMD impedance monitoring module. Z1 106 and Z2 110 should be distinguishable from each other and from an impedance seen by electrodes 14 and 16 when implanted, e.g. in contact with body fluid or tissue.

An example drive signal may be a square wave current in one example. An illustrative drive signal may have an amplitude of 2 uA and frequency of 8 kHz, though smaller or larger amplitude signals having higher or lower frequencies may be applied. Power-savings can be achieved by minimizing the duty cycle for applying the drive signal and utilizing a small stimulation current. The practice of pre-implant state detection techniques disclosed herein is not limited to a particular type of drive signal, which may vary between implementations. Drive signals having various amplitudes, wave shapes and duty cycles may be used.

Impedance ranges may be specified for Z1 106 and Z2 110 that do not overlap. Depending on the accuracy of the impedance monitoring circuit, the difference between the shipping impedance and the pending implant impedance may be larger or smaller. In one example, the difference in impedance between the shipping impedance and the pending implant impedance may be at least a 5-fold difference. The difference may be at least a 10-fold difference in other examples. To illustrate, Z1 106 may be in the range of approximately 50 to 100 kilo ohms, and Z2 110 may be in the range of approximately 5 to 10 kilo ohms. In some examples, the term "approximately" as used herein refers to a range of ±10% a stated value. In one example, an expected impedance upon IMD implantation may be approximately 2 kilo-ohms or less. Thus, the impedances associated with the various pre-implant states are selected to enable IMD 10 to easily discriminate between pre-implant states and optionally between a pre-implant state and an implant state. The pre-implant impedances may be at least 5 times greater than the expected maximum tissue impedance. If the maximum tissue impedance is expected to be approximately 2 kilo-ohms, then a pending-implant and a shipping impedance of 10 kilo-ohms and 50 kilo-ohms, respectively or vice versa, could be utilized. However, if the impedance monitoring circuit is sufficiently accurate, the difference in the impedance values between the shipping impedance and the pending implant impedance could be smaller, e.g., the shipping and pending implant impedances might be 6 kilo ohms and 8 kilo ohms, respectively.

In various examples, contacts 102, 104 and 106 may be implemented using metallic contacts coupled to known resistive elements, electrically conductive polymers formulated with specified impedances, or using conductive ink. Metallic contacts could include copper, gold, aluminum, platinum, iridium, titanium, stainless steel, nickel, or any other metal or metallic alloy or combinations thereof, which could be coupled to resistors embedded in the wall of enclosure 100 or mounted along an inner or outer surface of enclosure 100 and may be protected by an insulative coating or seal.

Conductive polymers may be formulated to have an impedance within a specified range and could be implemented to form contacts 102, 104, and 106 and/or the associated impedances Z1 106 and Z2 110. Conductive polymers can include inherently conductive polymers or non-conductive polymers filled with a conductive filler such as carbon black, stainless steel fibers, or other conductive additives. Additives and percentages thereof in the conductive polymer may be selected to achieve the desired impedance. Some examples of conductive polymers that could be used to form contacts 102, 104 and 106 or a portion of enclosure 100 are disclosed in commonly-assigned U.S. Pat. No. 7,512,447 (Marshall, et al.), incorporated herein by reference in its entirety.

Conductive ink may be formulated to have a controlled impedance and may be printed on a surface of enclosure 100 to form any portion of contacts 102, 104, 108 and associated impedances Z1 106 and Z2 110. Conductive inks formulated to have different specified impedances may be printed along enclosure 100 to form the different impedances Z1 106 and Z2 110. In some examples, conductive ink may be printed onto an inner surface of enclosure 100 to form contacts 102, 104 and 108 and standard electrical components or conductive polymers having specified impedances may be mounted between the contacts 102, 104 and 108 to form the respective impedances Z1 106 and Z2 110. Alternatively, conductive ink may be printed along a surface of enclosure 100 as a trace extending from contact 102 to contact 104 and as a trace extending from contact 102 to contact 108 to form the separate, distinguishable impedances Z1 106 and Z2 110. Additional embodiments of an enclosure including conductive ink and/or conductive polymers for establishing one or more known pre-implant impedances used for detecting pre-implant states are described below.

Figure 4A:
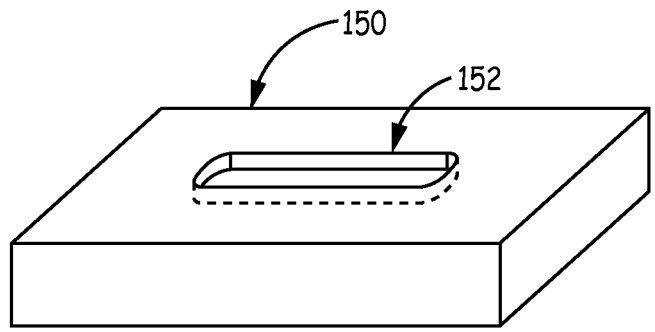
FIGS. 4A and 4B are schematic views of an enclosure according to one example.
Figure 4B:
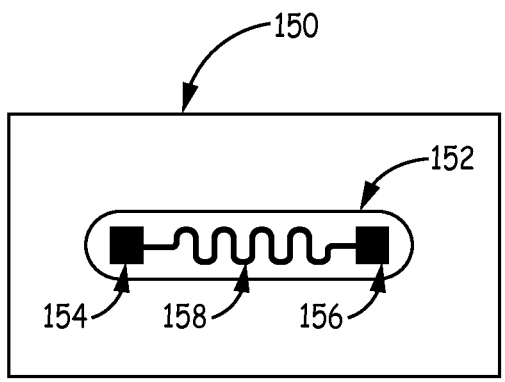

FIG. 4A is a schematic perspective view of an enclosure 150 according to one example. Enclosure 150 is a non-conductive polymer tray having a contoured, recessed surface 152 for receiving and retaining IMD 10 in a first, shipping position. As shown in FIG. 4B, contacts 154 and 156 are positioned along recessed surface 152 at spaced apart locations for mating with IMD electrodes 14 and 16. In one example, contacts 154 and 156 are printed conductive ink contacts. An electrically conductive path or trace 158 extends from contact 154 to contact 156 and defines a known electrical impedance between contacts 154 and 156 recognized by IMD 10 as the shipping impedance. The impedance of conductive path 158 is established by taking into consideration design factors including the conductivity of the ink, the overall path length and the path width. For example, the conductive path 158 may be a direct path or an indirect path that is longer than the shortest distance between contacts 154 and 156. Examples of indirect paths that may be used to achieve a desired path length and resulting impedance include sinusoidal, serpentine, spiral, or other repeating pattern.

Upon removal from tray 150, the impedance monitoring module 25 of IMD 10 measures an open-circuit impedance between electrodes 14 and 16. IMD 10 is configured to detect a pending-implant state upon measuring an open-circuit impedance after measuring the known impedance of contacts 154, 156 and path 158. In this example, therefore, the first electrical impedance measured to detect the first, shipping state is a specified shipping impedance between contacts 154 and 156 of enclosure 150 and the second electrical impedance measured to detect the second, pending-implant state is the open-circuit impedance that is present between IMD electrodes 14 and 16 when disconnected from contacts 154 and 156 and exposed to air.

Conversely, in some examples, tray 150 may be a test tray in which IMD 10 is inserted prior to a scheduled implant to test the operability of IMD 10. In this case, IMD 10 may be packaged with electrodes 14 and 16 exposed to air such that impedance monitoring module 25 measures an open-circuit impedance known by IMD 10 to be the shipping impedance. Upon measuring the impedance of contacts 154 and 156 and path 158, IMD 10 detects a pending-implant state.

Figure 5:
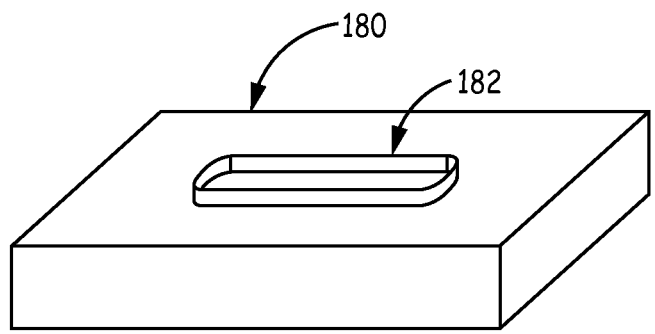
FIG. 5 is a schematic perspective view of an enclosure according to another example.

FIG. 5 is a schematic perspective view of an enclosure 180 according to another example. Enclosure 180 may be a uniformly conductive polymer material having a contoured recessed surface 182 for receiving and retaining IMD 10. Discrete "contacts" are not necessarily formed along surface 182 for interfacing with IMD electrodes 14 and 16. Rather, when IMD 10 is positioned in recess 182, electrodes 14 and 16 will be in direct contact with the surface of the conductive polymer material of tray 180 and measure the impedance of the conductive polymer. Alternatively, recessed surface 182 or only portions thereof are formed of a conductive polymer for contacting IMD electrodes 14 and 16 and remaining portions of tray 180 are formed of a different, non-conductive material.

The impedance of the conductive polymer may be known to IMD 10 as the shipping impedance and used to detect the first, shipping state; measurement of an open circuit impedance upon removal from tray 180 results in the detection of the pending implant state.

Alternatively, the IMD 10 electrodes may be exposed to air in an open circuit state in a shipping position and positioned against surface 182 to be coupled to the conductive polymer impedance during a pending-implant position. For example, IMD 10 may be packaged in tray 180 at a manufacturing facility with both electrodes 14 and 16 positioned facing upward, away from and not contacting tray 180 in a shipping position. A clinician or other user may turn IMD 10 over to face electrodes 14 and 16 down against and in electrical contact with surface 182 in a pending-implant position such that the impedance monitoring module 25 measures the impedance of the conductive polymer surface of tray 180 and detects the pending-implant state.

FIGS. 6A-6C are schematic diagrams of an enclosure in the form of an implant tool 200 that enables IMD 10 to detect a pending-implant state. FIGS. 6A-6C are sectional views of various stages or positions of the implant tool 200. As described above, IMD 10 includes an impedance monitoring module 25 that periodically measures the impedance between electrodes 14 and 16 to detect the shipping and pending-implant states of IMD 10 and control operation of IMD 10 accordingly. Each of the stages or positions within implant tool 200 present a different impedance between electrodes 14 and 16. IMD 10 is configured to identify each impedance associated with a particular position or stage and control IMD operation accordingly.

Implant tool 200 includes an outer body 202 and an advancement member 230. Outer body 202 has an inner lumen 206, defined by inner wall surface 208, for receiving and retaining IMD 10. Lumen 206 has a cross-sectional shape configured to accommodate the shape of IMD 10. Outer body 202 extends between a proximal handle 210 having a proximal opening 204 into inner lumen 206 for receiving advancement member 230 and a distal opening 212 defined by inner wall surface 208 through which IMD 10 may be loaded into and ejected from outer body 202.

In some examples, outer body 202 may be similar to a syringe body and advancement member 230 may be configured as a plunger advanceable through the syringe body. However, in other examples, and outer body of implant tool 200 may be configured as a catheter, introducer, or other delivery tool having an inner lumen that may or may not be fully enclosed by a luminal wall. An advancement member 230 may be configured as a push wire or other elongated tool configured to advance IMD 10 through the outer body 202. In various applications, implant tool 200 may be configured to implant IMD 10 in a subcutaneous, submuscular, intra-thoracic, intra-abdominal, intra-cardiac, intra-vascular, intra-cranial or any other internal body location.

Three contacts 214, 216 and 218 extend along inner wall surface 208. In one example, the first contact 214 is an elongated contact located nearest proximal handle 210. A second contact 216 is spaced apart distally from the first contact 214 to form a first contact pair having a first impedance 220. IMD 10 may be inserted or positioned at a first position within implant tool 200 at the time of manufacture or at the time of shipping, also referred to herein as a shipping position as shown in FIG. 6A. When IMD 10 is in a first pre-implant or shipping position, IMD electrodes 14 and 16 are in direct electrical contact with first contact 214 and second contact 216. IMD impedance monitoring module 25 measures the impedance between electrodes 14 and 16, determines that the measured impedance corresponds with or approximately matches shipping impedance 220, and IMD 10 operates in accordance with the shipping state. In the shipping state, IMD 10 may operate in a minimal power state with a majority of device circuitry powered down to minimize power consumption. As long as IMD 10 continues to measure impedance 220, IMD 10 operates in the shipping state.

Advancement member 230 includes a shaft 234 extending from a proximal handle 232 to a distal end 236 which may be contoured to mate with a proximal end of IMD 10 for advancing IMD 10 through outer body 202. Outer body 202 and advancement member 230 may be configured with interlocking or interfacing protruding and recessed surfaces which form locking mechanisms for holding the advancement member 230 and IMD 10 in the first, shipping position and in a second pending-implant position (shown in FIG. 6B). In FIG. 6B, advancement member 230 includes a first distal groove or notch 238a that interfaces with a protruding mechanical stop 224 extending from inner wall surface 208 of outer body 202 to form a stopping or locking mechanism. When advancement member 230 is advanced through outer body 202 until stop 224 interacts with notch 238a, IMD 10 and advancement member 230 are held in the first shipping or pre-implant position. The stopping mechanism of protruding stop 224 and distal notch 238a (or proximal notch 238b with respect to proximal handle 232) may also provide tactile feedback to a user when positioning IMD 10 in one of the two desired pre-implant positions, e.g., a first pre-implant or shipping position (as shown in FIG. 6A) and a second pending-implant position (as shown in FIG. 6B).

FIG. 6B is a sectional view of implant tool 200 when IMD 10 is advanced to the second pre-implant position or pending-implant position. A user may advance IMD 10 to the pending-implant position as shown using advancement member 232. Upon reaching the pending-implant position, the second, proximal notch 238b of advancement member 230 interfaces in an interlocking manner with protruding stop 224 to provide tactile feedback to the user that IMD 10 has been advanced to the pending-implant position and prevents advancement member 232, and subsequently IMD 10, from slipping out of the pending-implant position. In some instances, IMD 10 may interface with inner wall surface 208 to provide enough friction to prevent IMD 10 from slipping out of opening 212 without a forward force applied to advancement member 230. In other instances, distal end 236 of advancement member 230 may include a closure or an attachment mechanism to latch, clasp, fasten, hook, grasp, grip, hold, grapple or otherwise attach or connect to IMD 10 to prevent IMD 10 from slipping out of opening 212 without being released by the mechanism of advancement member 230.

In the pending-implant position, electrodes 14 and 16 of IMD 10 are in direct electrical contact with contacts 214 and 218. In this example, proximal first contact 214 is elongated such when IMD 10 is advanced through outer body 202, proximal electrode 14 advances along but remains electrically coupled to contact 214 while distal electrode 16 becomes coupled to the third contact 218, spaced apart distally from contact 216. First contact 214 and third contact 218 are characterized by the second, pending-implant impedance 222 that is different than the shipping impedance 220. As generally described previously in conjunction with FIGS. 3A and 3B, the respective impedances 220 and 222 corresponding to a shipping impedance and a pending-implant impedance applied between contacts 214 and 216 and between contacts 214 and 218, respectively, may vary between embodiments as long as the difference between impedance 220 and impedance 222 is large enough to be easily detectable and distinguishable by impedance monitoring module 25 of IMD 10.

After being moved to the second, pending-implant position, impedance monitoring module 25 of IMD 10 measures impedance 222 at the next impedance monitoring interval. As such, IMD 10 detects the pending-implant state when impedance monitoring module 25 measures the second impedance 222, between contacts 214 and 218, which is different than the first impedance 220 between contacts 214 and 216. In response to detecting the second impedance 222 associated with the pending-implant position, IMD 10 transitions to the pending-implant state. In the pending-implant state, IMD 10 may perform one or more operations in preparation for implantation. IMD 10 may, for example, transmit a pending implant confirmation signal indicating IMD 10 is verified to be operating properly. IMD 10 may wirelessly transmit the confirmation signal from communication module 24 to an external device (e.g., programmer, computer, handheld or other device). In other embodiments, IMD 10 may alternatively or additionally provide the confirmation signal as an audible, visual or tactile signal (e.g., audible tone, a vibration, or an LED that illuminates) upon electrical connection to the second pair of contacts 214 and 218.

In this way, the clinician is notified that the IMD 10 is fully operable and in satisfactory condition for implantation. If the pending-implant confirmation signal is not received by the external device or the audible, visual or tactile signal is not generated upon adjusting IMD 10 from the first, shipping position to the second, pending-implant position, this may be an indication that the IMD 10 is not operating satisfactorily for implantation. The clinician may select a different device to implant or postpone the surgical procedure prior to starting surgery.

IMD 10 may perform additional operations, such as self-diagnostic tests which may include a battery test, a memory check, or other tests prior to sending the confirmation signal. The confirmation signal may include the results of any of the self-diagnostic tests.

Both the shipping state and the pending-implant state may be referred to as pre-implant states since the IMD 10 is not fully powered and performing its primary functions, such as the intended physiological monitoring functions. As such the pending-implant state may still be a minimally powered state or reduced powered state as compared to the fully operational implant state since only the operations of transmitting a confirmation signal and any optional self-diagnostic tests need be performed.

After transmitting the confirmation signal, IMD 10 may return to a minimally powered or off state and remain in that state while residing in the second, pending-implant position within implant tool 200. As such, IMD 10 will not utilize additional power transmitting subsequent confirmation signals. Alternatively, the IMD 10 may transmit a periodic "implant-ready" signal after transmitting the initial pending-implant confirmation signal while still in the pending-implant position to notify the clinician that the IMD 10 remains in operable condition and is ready for implantation.

It is contemplated that in some instances, the pending-implant state may be the fully functional, normal operating state. In this case, the IMD 10 is powered up to the normal operating state to begin monitoring and/or therapy delivery operations according to pre-programmed algorithms upon detecting the pending-implant impedance 222.

If the implant procedure is cancelled or delayed, IMD 10 may be returned to the first, shipping position within implant tool 200 in some examples. In such an instance, IMD 10 determines that the impedance corresponds to the shipping impedance at the next impedance check and transitions back to the shipping state. When subsequently advanced again to the second, pending-implant position, IMD 10 may again transmit the confirmation signal to notify the clinician that the IMD 10 is in operable condition, including passing any of the optional self-diagnostic tests, and ready for implantation.

FIG. 6C is a sectional view of implant tool 200 and IMD 10 in a fully advanced implant position. Advancement member 230 is advanced to eject IMD 10 through outer body distal opening 212. Advancement member distal end 236 has a contoured distal end surface 240 for interfacing with the proximal end surface 15 of IMD 10. Outer body handle 210 acts as a proximal stop for advancement member handle 232 to prevent over-advancement of member 230 through outer body 202. In instances in which the distal end 236 of advancement member 230 includes a distal closure or an attachment mechanism, the closure or attachment mechanism may be automatically or manually actuated to release IMD 10 upon reaching the fully advanced position.

In the embodiment shown in FIGS. 6A-6C, the protruding stop 224 included in the stopping/locking mechanism of outer body 202 for interacting with notches 238a and 238b in advancement member 230 in the shipping and pending-implant positions (as shown in FIGS. 6A and 6B respectively) is pushed outward from lumen 206 by shaft 234. Protruding stop 224 extends from a flexible beam 242 formed in the wall of outer body 202. Protruding stop 224 is free to flex inward when aligned with a notch 238a or 238b but flexes outward (into the wall of outer body 202) when interacting with shaft 234 as advancement member 230 is advanced. Alternative advancement members with stopping mechanisms that interface with outer body 202 for providing tactile feedback to a user and for maintaining the position of advancement member 230 and IMD 10 at a desired shipping or pending-implant location within outer body 202 may include ridges, flanges, threads, ratchets, or other protruding members configured to mate with grooves, cavities, recesses or indentations. In some embodiments, the IMD electrodes 14 and 16 and/or the contacts 214, 216 and 218 may be a component of or include a recessed feature or a protruding feature of the interlocking stopping mechanism. Moreover, other mechanical structures may be used for extending and retracting IMD 10 into the various positions. For example, instead of an advancement member 230, implant tool 200 may include a mechanical structure in which a trigger, lever, actuator or other input mechanism causes IMD 10 to move to the various positions.

Upon ejection from outer body 202 into a desired implant site, IMD electrodes 14 and 16 will be exposed to body tissue and fluids. Impedance monitoring module 25 may be configured to detect another change in impedance corresponding to the impedance in the body tissue and/or fluid. The impedance between electrodes 14 and 16 when implanted must be distinguishable from impedances 220 and 222 in this case.

In response to measuring an impedance determined to be the fully functional implant state, IMD 10 may transition to fully-powered, normal operations according to an implant state. The implant state corresponds with the normal operating mode of IMD 10. If the self-diagnostic tests were not performed in the pending-implant state, IMD 10 may perform self-diagnostic testing as part of the implant state. Additionally, IMD 10 begins to acquire physiological signals, process those signals, and transmit the signals in accordance with pre-programmed operating parameters while operating in the implant state. Additionally, any therapy provided as part of the normal operating mode will also be initiated. The normal operation initiated upon detecting implantation of IMD 10 will vary between embodiments, according to the particular medical application for which IMD 10 is being used.

Accordingly, IMD 10 may be readily adjusted between at least two pre-implant states by shifting a position of IMD 10 between a shipping position corresponding to a first known impedance and a pending-implant position corresponding to a second known impedance that is significantly different than the first known impedance. IMD 10 can be further adjusted to an implant state upon determining an implant position corresponding to an impedance that is significantly different than the first and second known impedances.

The illustrative embodiments shown in FIGS. 6A-6C include three contacts forming two pairs of contacts having distinct electrical impedances. It is contemplated that an enclosure may be configured with two or more separate pairs of contacts, e.g., a total of at least four contacts rather than three, such that the IMD 10 is in contact with a first pair of contacts in the shipping position and a second pair of contacts in the pending-implant position with no contacts shared between the two pairs.

It is further contemplated that an enclosure providing two pairs of contacts defining a respective shipping impedance and a pending-implant impedance may be a multi-component enclosure. For example, the IMD 10 may be packaged in a shipping enclosure similar to the enclosures illustrated in FIGS. 3A through 5 having a first pair of contacts or surface characterized by the shipping impedance. The IMD 10 may then be removed from the shipping enclosure and positioned into a pending-implant enclosure, which may be an implant tool similar to implant tool 200 of FIGS. 6A-6C, or simply a pre-implant test enclosure similar to the trays shown in FIGS. 4 and 5, having a surface with a second pending-implant impedance. The IMD 10 is capable of detecting a pending implant state by detecting a change from the shipping impedance to the pending-implant impedance when removed from the shipping enclosure and properly positioned into the implant tool or other second part of a two part enclosure such that the IMD electrodes are in direct electrical contact with the second pair of contacts. Accordingly, various embodiments may include two or more pairs of contacts defined by three or more individual contacts, which may or may not include shared contacts between individual pairs of contacts. In some embodiments, a surface contacting IMD 10 electrodes has a pre-implant impedance without discrete contacts positioned along the surface (such as the enclosure 180 of FIG. 5). The contacts or surfaces having known pre-implant impedances may be positioned along one or more enclosure components used for carrying, retaining, and/or implanting the IMD to enable detection of a pending-implant state to confirm operability of the IMD, e.g. prior to starting a surgical procedure.

Figure 7:
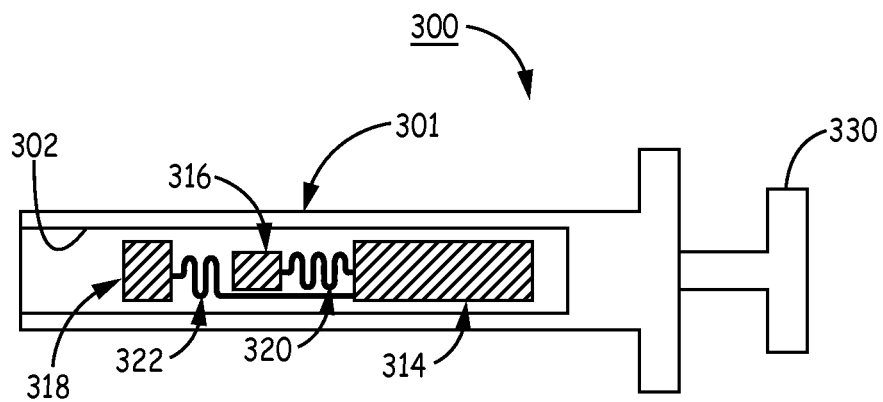
FIG. 7 is a schematic sectional view of one example of an implant tool having a shipping impedance and a pending-implant impedance.

FIG. 7 is a schematic sectional view of one example of an implant tool 300 having a shipping impedance and a pending-implant impedance. Tool 300 includes an outer body 301 and an advancement member 330 for advancing IMD 10 from a shipping position to a pending implant position within tool 300 as generally described above in conjunction with FIGS. 6A-6C.

Outer body 301 has an inner surface 302 that defines an inner lumen or cavity for receiving and retaining IMD 10 prior to implantation. Three contacts 314, 316 and 318 are printed along inner surface 302 using conductive ink. Contacts 314 and 316 are electrically connected to each other by a conductive trace or path 320, some or all of which may be printed using conductive ink. The pair of contacts 314 and 316 and associated conductive path 320 define a shipping impedance presented to IMD 10 when it is positioned with electrodes 14 and 16 against contacts 314 and 316. IMD 10 detects the shipping state when positioned within tool 300 with electrodes 14 and 16 in electrical contact with contacts 314 and 316.

Contacts 314 and 318 are connected by an electrically conductive path 322, some or all of which may be printed using conductive ink. The pair of contacts 314 and 318 and associated conductive path 322 define a pending-implant impedance presented to IMD 10 when it is positioned with electrodes 14 and 16 against contacts 314 and 318. Contact 314 is shown having a greater length than contacts 316 and 318 such that when IMD 10 is advanced within tool 300, a proximal electrode 14 may remain electrically coupled to contact 314 while distal electrode 16 is advanced from contact 316 to contact 318. IMD 10 detects the pending-implant state when IMD 10 is advanced within tool 300 such that electrodes 14 and 16 are in electrical contact with contacts 314 and 318.

A specified shipping impedance defined by contacts 314, 316 and conductive path 320 may be realized by selecting an ink with a desired impedance, printing a desired length of conductive path 320 and other design factors. The overall length of conductive path 320 may be made longer than the actual distance between contacts 314 and 316 by printing path 320 with a repeating pattern or other indirect pathway. A specified pending-implant impedance, different than the shipping impedance, and defined by contacts 314, 318 and conductive path 322 may be achieved by using an ink having a different conductivity for printing contact 318 than for printing contact 316, by using an ink having a different conductivity for printing path 322 than the ink used for printing path 320, or by printing path 322 with a different overall length and/or width than path 320. In other embodiments, contacts 314, 316, and 318 may include conductive metals and/or conductive polymers and be coupled by paths 320 and 322 printed using conductive ink(s).

Figure 8:
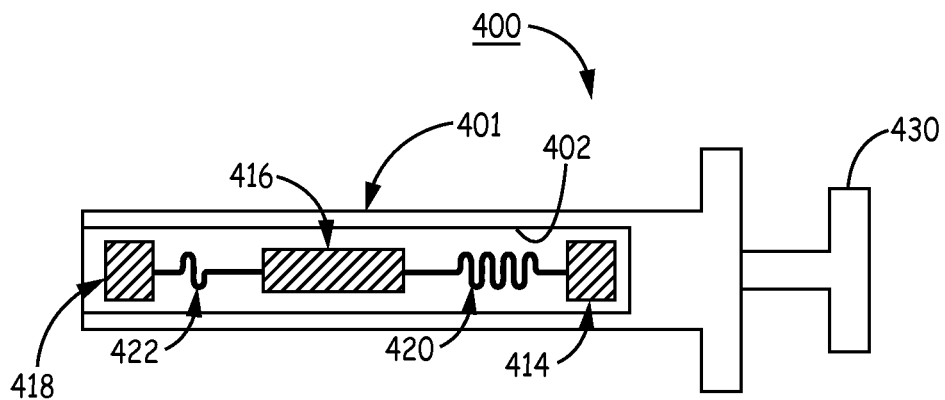
FIG. 8 is a schematic sectional view of another example of an implant tool having a shipping impedance and a pending-implant impedance.

FIG. 8 is a schematic sectional view of another example of an implant tool 400 having a shipping impedance and a pending-implant impedance. Tool 400 includes an outer body 401 and advancement member 430 for advancing IMD 10 from a shipping position to an implant position within outer body 401 as described above. Outer body 401 has an inner surface 402 defining an open lumen or cavity for carrying IMD 10. Three contacts 414, 416, and 418 define two pairs of contacts and associated impedances. Contacts 414 and 416 are connected by an electrically conductive path 420 which presents the shipping impedance to IMD 10 when IMD electrodes 14 and 16 are positioned in direct contact with contacts 414 and 416.

Contacts 416 and 418 are connected by a second electrically conductive path 422 having a different impedance than path 420. When IMD 10 is advanced within outer body 401 to a position with electrodes 14 and 16 in direct contact with contacts 416 and 418, the pending-implant impedance associated with path 422 is presented to IMD 10.

As described above, contacts 414, 416 and 418 and paths 420 and 422 may be printed along inner surface 402 using conductive ink. The two different shipping and pending-implant impedances may be realized by printing paths 420 and 422 with different lengths, different inks, and or different widths. A desired overall length of each trace 420 and 422 is achieved by printing traces 420 and 422 in a serpentine pattern, for example.

In the example shown in FIG. 8, the center contact 416 has a longitudinal length, which is the dimension extending along a longitudinal axis, e.g. a central long axis, of outer body 401, greater than its width. Though not required, the longitudinal length of contact 416 is shown to be greater than the longitudinal lengths of contacts 414 and 418 such that as IMD 10 is advanced through outer body 401 one or the other of electrodes 14 and 16 will be against contact 416 in both the shipping and pending-implant positions. In the shipping position, IMD electrode 14 will be against proximal contact 414, and IMD electrode 16 will be against center contact 416. Upon advancement to the pending-implant position, IMD electrode 14 is positioned against center contact 416, and IMD distal electrode 16 is positioned against distal contact 418. In other examples including three contacts for establishing two pairs of contacts each with an associated impedance, the distal contact 418 may be provided as the longest contact such that the distal electrode 16 of IMD 10 is against the distal contact 418 in both the shipping and pending-implant positions and the proximal IMD electrode 14 is against proximal contact 414 in the shipping position and the center contact 416 in the pending-implant position.

Figure 9:
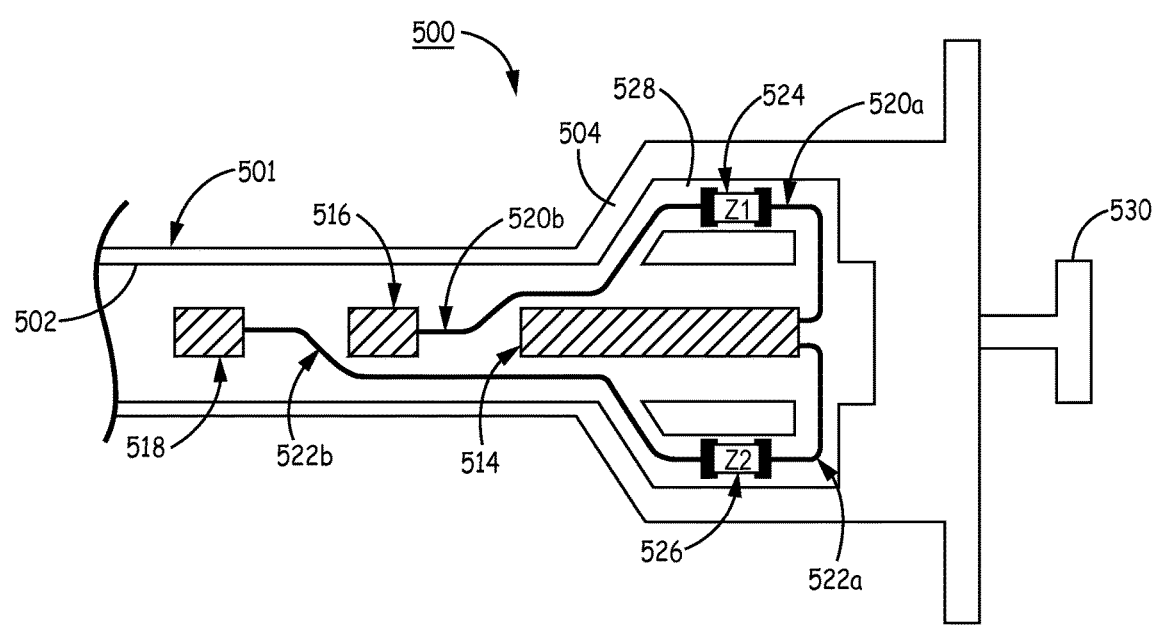
FIG. 9 is a side sectional view of an implant tool having a shipping impedance and a pending-implant impedance according to another example.

FIG. 9 is a sectional view of an implant tool 500 having a shipping impedance and a pending-implant impedance according to yet another example. Tool 500 includes an outer body 501 and advancement member 530. Tool 500 is configured for carrying and retaining IMD 10 in a shipping position and in a pending-implant position, for example as described in conjunction with the implant tool 200 shown in FIGS. 6A-6C. In this example, outer body 501 has, along its inner surface 502, a first pair of contacts 514 and 516 connected by an electrically conductive pathway including traces 520a and 520b and electrical component 524. Traces 520a, 520b and electrical component 524 define the shipping impedance. The second pair of contacts 514 and 518 are connected by an electrically conductive pathway including traces 522a, 522b and electrical component 526, which define the pending-implant impedance.

Contacts 514, 516 and 518 and traces 520a, 520b, 522a and 522b may be printed along inner surface 502 using a conductive ink. The distinct shipping and pending-implant impedances are realized by coupling different electrical components 524 and 526 between the two different pairs of contacts 514, 516 and contacts 514, 518, respectively. Electrical components 524 and 526 may be surface mount resistors in one example. Other discrete components or combinations of multiple components may be coupled to traces 520a, 520b and 522a, 522b for establishing distinct shipping and pending-implant impedances.

The outer body wall 504 may include pockets or cavities 528, which may be along a widened portion of outer body 501, in which electrical components 524 and 526 may be positioned without impeding advancement of IMD 10 and advancement member 530 through tool 500. Alternatively, inner surface 502 may be contoured to form cavities in which electrical components 524 and 526 are mounted and then sealed over with an epoxy or other insulative, protective layer.

Figure 10:
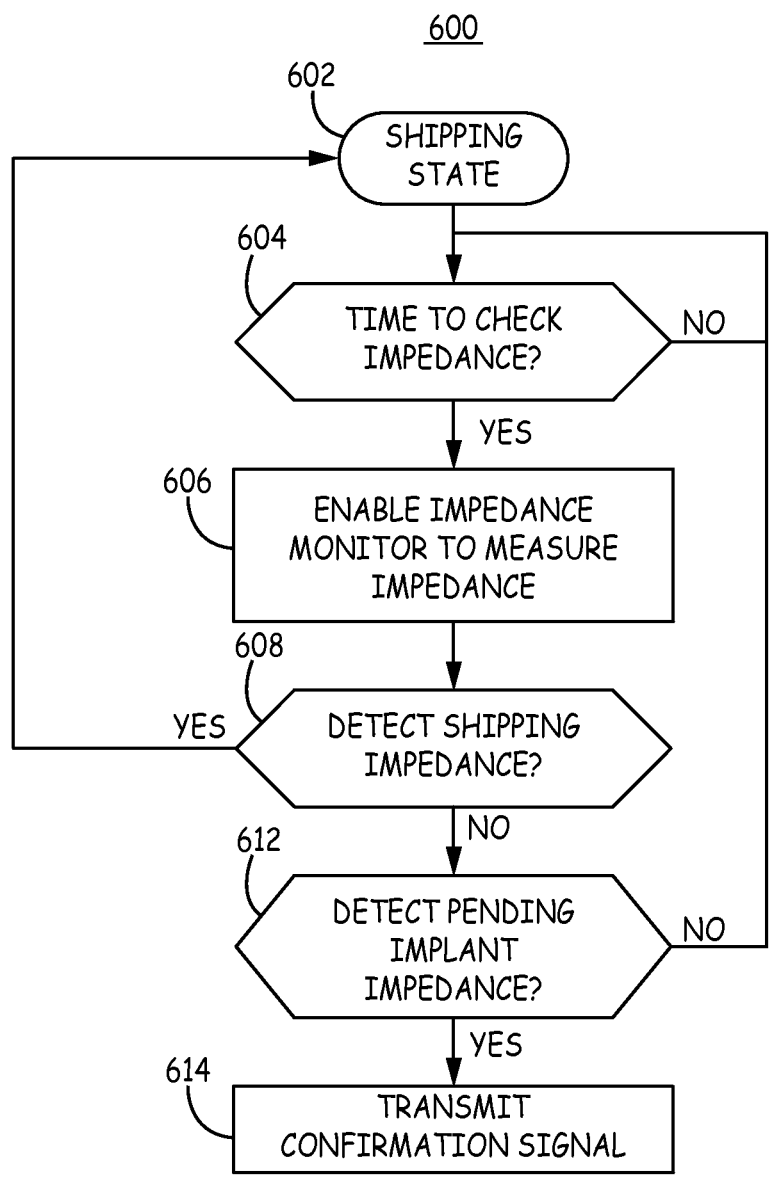
FIG. 10 is a flow chart of a method for adjusting the operation of an IMD based on monitoring impedance between IMD electrodes prior to implantation of the IMD.

FIG. 10 is a flow chart 600 of a method for adjusting the operation of an IMD based on monitoring the impedance between IMD electrodes prior to implantation of the IMD in a patient's body. An IMD is initially in a minimally powered shipping state as indicated at block 602. If an impedance monitoring interval expires, according to an internal clock or timer, as determined at block 604, the IMD processor and control module powers up the impedance monitoring module to measure impedance at block 606. If a known shipping impedance is detected due to the IMD electrodes being exposed to an open-circuit condition or positioned against an enclosure surface characterized by a first, shipping impedance, the IMD remains in the shipping state and waits for the next impedance monitoring interval to expire by returning to block 604.

If the shipping impedance is not detected at block 608, and the pending-implant impedance is detected due to the IMD electrodes being positioned against an enclosure surface characterized by a second, pending-implant impedance, or exposed to an open-circuit condition when the shipping impedance is different than the open circuit condition, the IMD telemetry module is enabled to transmit a pending-implant confirmation signal at block 614. The IMD may transmit a continuous or intermittent confirmation signal as long as the pending-implant impedance is detected. In other embodiments, the IMD transmits a single confirmation signal.

In some instances, the impedance monitoring module may not detect either of the shipping or the pending-implant impedances, e.g. during a transition between the two known impedances. If neither of the impedances is detected, the IMD may remain in the current pre-implant state, the shipping or the pending-implant state, until the next impedance monitoring interval expires.

After transmitting the confirmation signal, the pre-implant state detection process may be complete. In other embodiments, after detecting the pending-implant state, the impedance monitoring module may continuously monitor for an impedance associated with implantation in contact with body tissue or fluids. In some embodiments, the impedance monitoring module may monitor the impedance at the IMD electrodes at an increased monitoring frequency to detect an implant state or a change back to the shipping impedance. Alternatively, after transmitting the confirmation signal, the IMD may return to the minimal power state and wait for the next scheduled impedance monitoring check at block 602 and repeat the operations of blocks 602 through 614 until an implant impedance is detected.

Thus, a method and apparatus for detecting various pre-implant states of an IMD have generally been presented in the foregoing description with reference to specific embodiments. Various examples described herein may be combined in any combination other than the illustrative examples presented and some aspects may be added or omitted without departing from the scope of the disclosure. Methods for detecting various pre-implant states may include steps performed in a different order or combination than the illustrative examples shown and described herein. It is appreciated that various modifications to the referenced embodiments may be made without departing from the scope of the disclosure as set forth in the following claims.

The invention claimed is:

1. A medical device system, comprising:
   an implantable medical device comprising:
      a first electrode;
      a second electrode;
      an impedance monitoring module coupled to the first electrode and the second electrode and configured to measure an impedance between the first electrode and the second electrode; and
      a control module configured to control operation of the implantable medical device based on the measured impedance; and
   an enclosure for carrying the implantable medical device, the enclosure comprising a surface having an electrical impedance and configured to contact the first electrode and the second electrode when the implantable medical device is placed within the enclosure,
   wherein the control module is configured to detect one of a first pre-implant state and a second pre-implant state of the implantable medical device in response to the impedance monitoring module detecting a change in impedance between the first electrode and the second electrode and adjust operation of the implantable medical device in response to detecting the impedance change.

2. The system of claim 1, wherein the implantable medical device further comprises a telemetry module configured to transmit wireless communications,
   wherein the control module is configured to control the telemetry module to transmit a signal in response to the detection of the change in impedance.

3. The system of claim 2, wherein the telemetry module comprises a transmitter without a receiver such that the implantable medical device is configured for uni-directional, transmission communication only.

4. The system of claim 1, wherein the surface comprises:
   a first pair of contacts having a first electrical impedance, wherein a first contact of the first pair of contacts is configured to contact the first electrode of the implantable medical device and a second contact of the first pair of contacts is configured to contact the second electrode of the implantable medical device when the implantable medical device is placed in a first position within the enclosure; and
   a second pair of contacts having a second electrical impedance different than the first electrical impedance, wherein a first contact of the second pair of contacts is configured to contact the first electrode of the implantable medical device and a second contact of the second pair of contacts is configured to contact the second electrode of the implantable medical device when the implantable medical device is placed in a second position within the enclosure.

5. The system of claim 4, wherein the enclosure comprises an advancement member configured to advance the implantable medical device from the first position to the second position.

6. The system of claim 4, wherein the enclosure comprises a stopping member for controlling advancement of the implantable medical device from the first position to the second position.

7. The system of claim 5, wherein the enclosure comprises:
   an outer body, the surface defining an inner lumen of the outer body, the inner lumen configured to receive the implantable medical device; and
   wherein the advancement member comprises a plunger configured to advance within the inner lumen to advance the implantable medical device from the first position to the second position.

8. The system of claim 4, wherein:
   the first contact of the first pair of contacts extends along a portion of the enclosure;
   the second contact of the first pair of contacts being spaced apart from the first contact;

the first contact of the second pair of contacts being the first contact of the first pair of contacts; and the second contact of the second pair of contacts being spaced apart from the second contact of the first pair of contacts.

9. The system of claim 4, wherein the first contact of the first pair of contacts has a first longitudinal length along the enclosure, the second contact of the first pair of contacts has a second longitudinal length along the enclosure, and the second contact of the second pair of contacts has a third longitudinal length along the enclosure, the first longitudinal length being greater than the second and third longitudinal lengths.

10. The system of claim 4, wherein the enclosure comprises a locking mechanism adjustable between a first locking position to maintain the implantable medical device in a first position coupled to the first pair of contacts and a second locking position to maintain the implantable medical device in a second position coupled to the second pair of contacts.

11. The system of claim 1, wherein the surface comprises a conductive polymer.

12. The system of claim 1, wherein the surface comprises a conductive ink.

13. The system of claim 1, wherein the enclosure comprises a first component for retaining the implantable medical device in a first position along a portion of the surface having a first impedance and a second component for retaining the implantable medical device in a second position along a portion of the surface having a second impedance.

14. The system of claim 1, wherein the control module is configured to detect the one of the first pre-implant state and the second pre-implant state in response to the impedance monitoring module detecting a change between the impedance of the surface and an open circuit impedance.

15. A method for verifying an implantable medical device status prior to implantation, comprising:

monitoring an impedance between a pair of electrodes of the implantable medical device;

detecting a change in the impedance between the pair of electrodes when a position of the implantable medical device is changed relative to a surface of an enclosure for carrying the implantable medical device, the enclosure comprising a surface having an electrical impedance and configured to contact the first electrode and the second electrode when the implantable medical device is placed within the enclosure;

detecting one of a first pre-implant state and a second pre-implant state of the implantable medical device in response to detecting the change in impedance between the first electrode and the second electrode; and adjusting operation of the implantable medical device in response to detecting the change in impedance.

16. The method of claim 15, further comprising, responsive to detecting the impedance change transmitting a wireless communication signal from the implantable medical device.

17. The method of claim 16, wherein transmitting the wireless communication signal comprises only uni-directional, transmission communication.

18. The method of claim 15, wherein detecting the change in impedance between the first electrode and the second electrode comprises detecting a change from a first impedance of the enclosure to a second impedance of the enclosure, the first impedance defined by a first pair of contacts along the surface of the enclosure, a first contact of the first pair of contacts configured to contact the first electrode of the implantable medical device and a second contact of the first pair of contacts configured to contact the second electrode of the implantable medical device when the implantable medical device is placed in a first position within the enclosure, the second impedance defined by a second pair of contacts along the surface of the enclosure and different than the first impedance, a first contact of the second pair of contacts configured to contact the first electrode of the implantable medical device and a second contact of the second pair of contacts configured to contact the second electrode of the implantable medical device when the implantable medical device is placed in a second position within the enclosure.

19. The method of claim 18, further comprising advancing the implantable medical device from the first position within the enclosure to the second position within the enclosure.

20. The method of claim 19, wherein advancing the implantable medical device to the second position comprises advancing the implantable medical device from the first position to the second position held by a stopping mechanism.

21. The method of claim 19, wherein the advancing comprises advancing a plunger through an inner lumen of an outer body of the enclosure, the surface being the inner lumen.

22. The method of claim 19, wherein advancing the implantable medical device from the first position to the second position comprises:

advancing the first electrode from a first position along the first contact of the first pair of contacts to a second position along the first contact of the first pair of contacts, the first contact of the first pair of contacts also being the first contact of the second pair of contacts; and advancing the second electrode from the second contact of the first pair of contacts to the second contact of the second pair of contacts, the second contact of the first pair of contacts and the second contact of the second pair of contacts being spaced apart from the first contact.

23. The method of claim 18, further comprising adjusting a locking mechanism of the enclosure between a first locking position to maintain the implantable medical device in a first position coupled to the first pair of contacts and a second locking position to maintain the implantable medical device in a second position coupled to the second pair of contacts.

24. The method of claim 15, wherein measuring the impedance comprises measuring the impedance through a conductive polymer of the enclosure.

25. The method of claim 15, wherein measuring the impedance comprises measuring the impedance through a conductive ink printed along the surface.

26. The method of claim 15, wherein detecting the change in impedance comprises:

detecting a change from a first impedance of a first portion of the surface of the enclosure to a second impedance of a second portion of the surface of the enclosure, the enclosure comprising a first component for retaining the implantable medical device in a first position along the first portion of the surface having the first impedance and a second component for retaining the implantable medical device in a second position along the second portion of the surface having the second impedance.

27. The method of claim 15, wherein detecting the impedance change comprises detecting a change between the impedance of the surface and an open circuit impedance.

28. An implantable medical device system, comprising:
means for monitoring impedance between a first electrode and a second electrode of an implantable medical device;
means for coupling a first impedance to the first electrode and the second electrode and a second impedance to the first electrode and the second electrode prior to implanting the implantable medical device;
means for detecting an impedance change between the first impedance and the second impedance; and
means for controlling operation of the implantable medical device based on detecting the impedance change.

29. A non-transitory, computer-readable storage medium storing a set of instructions, which when executed by a control module of an implantable medical device causes the device to:

monitor an impedance between a pair of electrodes by an impedance monitoring circuit of the implantable medical device;
detect a change in the impedance between the pair of electrodes when a position of the implantable medical device is changed relative to a surface of an enclosure for carrying the implantable medical device, the enclosure comprising a surface having an electrical impedance and configured to contact the first electrode and the second electrode when the implantable medical device is placed within the enclosure;
detect one of a first pre-implant state and a second pre-implant state of the implantable medical device in response to the impedance monitoring module detecting the change in impedance between the first electrode and the second electrode; and
adjust operation of the implantable medical device in response to detecting the change in impedance.

* * * * *